United States Patent
Haras (10) Patent No.: US 8,358,874 B2
(45) Date of Patent: Jan. 22, 2013

(54) METHOD FOR DISPLAYING COMPUTED-TOMOGRAPHY SCANS, AND A COMPUTED-TOMOGRAPHY SYSTEM OR COMPUTED-TOMOGRAPHY SYSTEM ASSEMBLY FOR CARRYING OUT THIS METHOD

(75) Inventor: Gabriel Haras, Mücke (DE)

(73) Assignee: Siemens Aktiengesellschaft, Munich (DE)

( * ) Notice: Subject to any disclaimer, the term of this patent is extended or adjusted under 35 U.S.C. 154(b) by 1039 days.

(21) Appl. No.: 12/000,476

(22) Filed: Dec. 13, 2007

(65) Prior Publication Data
US 2008/0212862 A1  Sep. 4, 2008

(30) Foreign Application Priority Data
Dec. 13, 2006 (DE) .......................... 10 2006 058 906

(51) Int. Cl.
G06K 9/32 (2006.01)
G06K 9/00 (2006.01)
A61B 5/05 (2006.01)

(52) U.S. Cl. ........ 382/294; 382/128; 382/131; 382/132; 600/407

(58) Field of Classification Search .................. None
See application file for complete search history.

(56) References Cited

U.S. PATENT DOCUMENTS

| | | | | |
|---|---|---|---|---|
| 6,149,592 A * | 11/2000 | Yanof et al. | .................... | 600/427 |
| 6,320,931 B1 * | 11/2001 | Arnold | ............................. | 378/56 |
| 7,327,872 B2 * | 2/2008 | Vaillant et al. | ................ | 382/154 |
| 7,611,452 B2 * | 11/2009 | Allison et al. | .................... | 600/1 |
| 7,639,896 B2 * | 12/2009 | Sun et al. | ....................... | 382/294 |
| 7,822,241 B2 * | 10/2010 | Eck et al. | ....................... | 382/128 |
| 8,145,012 B2 * | 3/2012 | Meetz et al. | .................. | 382/294 |
| 2004/0114706 A1 * | 6/2004 | Ikeda et al. | ....................... | 378/4 |
| 2005/0135707 A1 * | 6/2005 | Turek et al. | ................... | 382/294 |
| 2007/0003016 A1 * | 1/2007 | Brunner et al. | ............ | 378/98.12 |

FOREIGN PATENT DOCUMENTS

DE  102005030646  1/2007

OTHER PUBLICATIONS

Lin, K-P., et al.; A General Technique for Interstudy Registration of Multifunction and Multimodality Images; 1994; IEEE Trans. on Nuclear Medicine; 41(6); pp. 1106-1110.*
Pluim et al.; Mutual-Information-Based registration of Medical Images: A Survey; 2003; IEEE Trans. on Medical Imaging, 22(8); pp. 986-1004.*

(Continued)

*Primary Examiner* — Tom Y Lu
*Assistant Examiner* — Thomas Conway
(74) *Attorney, Agent, or Firm* — Harness, Dickey & Pierce, P.L.C.

(57) ABSTRACT

At least one embodiment of the invention relates to a method and/or a computed-tomography system and/or a computed-tomography system assembly for displaying tomographic records, with a first computed-tomography display data record displaying structures of a first type and of a second type by way of a complex recording technique, with an area of interest with structures of a second type being marked there and with relative positions of the structures being determined, with a second computed-tomography display data record subsequently being created by a simpler recording technique, in which only structures of the first type can be identified, and the structures of the second type are made visible in this display on the basis of the known relative positions with respect to the visible structures of the first type or at least their position, or a surrounding boundary.

20 Claims, 3 Drawing Sheets

OTHER PUBLICATIONS

Maintz, J.B.A., et al.; A survey of medical image registration; 1998; Medical Image Analysis; 2(1); pp. 1-36.*

German Office Action issued Sep. 5, 2007.

* cited by examiner

METHOD FOR DISPLAYING COMPUTED-TOMOGRAPHY SCANS, AND A COMPUTED-TOMOGRAPHY SYSTEM OR COMPUTED-TOMOGRAPHY SYSTEM ASSEMBLY FOR CARRYING OUT THIS METHOD

PRIORITY STATEMENT

The present application hereby claims priority under 35 U.S.C. §119 on German patent application number DE 10 2006 058 906.8 filed Dec. 13, 2006, the entire contents of which is hereby incorporated herein by reference.

FIELD

Embodiments of the invention generally relate to a method for displaying computed-tomography records, and/or to a computed-tomography system or computed-tomography system assembly for carrying out this method. In at least one embodiment, position information is determined from a computed-tomography display data record in which structures of a first and second type including their relative positions with respect to one another are determined, and structures of a first type are determined later using a recording technique which places less load on the object being examined, and the structures of the second type are located on the basis of these identifiable structures.

BACKGROUND

It is generally known for scans to be carried out using relatively complex recording techniques, for example using contrast agent or using different X-ray energies, before computed-tomography-based interventions, in order to better identify structures which are difficult to identify, such as lesions in soft tissue parts. During the subsequent intervention, current computed-tomography imaging is then carried out in circumstances in which the load is reduced, since this examination in its own right generally produces a high dose because of the relatively long duration, with important additional information such as differences between soft parts being lacking in these circumstances.

Particularly when examining organs, for example a liver, it is particular difficult to distinguish between organ tissue, tumor tissue and vessels, so that complex examination methods which may result in a high patient dose, specifically the additional giving of contrast agents or the use of different spectra for the CT scan or else the use of a higher dose in order to improve the imaging, are used. Computed-tomography displays are then created using methods with lower doses during the subsequently carried out intervention, in which displays, for example, an originally identified tumor cannot be seen.

The problem is now to also obtain three-dimensional information about the position and size of a lesion during the planning examinations that are carried out first of all, and this information must be transferred to the displays during the actual intervention. Until now, this has been done by the user defining the position and orientation of a region of interest (ROI), that is to say of lesions, tumor tissues or regions which must not be injured, such as blood vessels, possibly with the assistance of landmarks, with these being transferred in an imaginary form to the scans during actual intervention on the basis of memory or, in an improved variant, by actual image comparison. On the one hand, this can lead to serious errors while on the other hand it places additional load on the user and represents a distraction from his actual task during the intervention.

It is also known for a previous image from the planning examination to be superimposed as a translucent image on the current scan and, if appropriate, to be shifted to produce as good a match as possible with the current scan during the intervention in order that the position of the ROI can be transferred as well as possible. When using a method such as this, one problem is that the entire scan has the planning examination scan superimposed on it, resulting in the current imaging process being in the background, as a result of which any changes in the current scan are overlooked.

SUMMARY

In at least one embodiment of the invention a method and a computed-tomography system, or an assembly of different computed-tomography systems, is developed which allows a safe display of the region of interest with less interference with the new image.

The inventor has found, in at least one embodiment, that it is possible when carrying out computed-tomography scans to distinguish between structures of a first type and a second type by using different techniques, with structures of the first type representing structures which are identified without any problems in both recording techniques, while structures of the second type are those structures which can be identified only in the more complex recording technique. Since the structures of the first type are present in both recording techniques, it is possible to use these structures as position marks, with the structures of the second type being mapped relative to these positions, that is to say their relative position can thus be determined two-dimensionally or three-dimensionally. In a corresponding manner, during scans in which only structures of the first type can be identified, these structures or else appropriately marked areas are transferred accurately in position to displays which show only the structures of the first type. If only these structures or marked regions are transferred to the current images, which actually have less detail, then this has virtually no adverse effect on the identification capability in these current images.

According to at least one embodiment of the invention, for example, planning scans can first of all be created using complex methods which may also result in a relatively high dose for the patient, and structures from these planning scans are transferred to current scans with considerably less detail, created during an intervention. In particular, this even allows fundamentally different recording techniques to be combined, such as CT scans with one or more energy spectra, PET scans or combinations of PET with CT or MRI scans or pure MRI scans. This also makes it possible to use an X-ray C-arc system during the intervention, which is particularly advantageous in terms of the space available for a doctor carrying out a treatment and, possibly, personnel who need to be adjacent to the patient.

On the basis of this inventive idea, the inventor, in at least one embodiment, proposes that the problem be solved by a method for displaying computed-tomography scans, comprising:

generation of a first display data record using a first recording technique and of at least one second computed-tomography display data record using a second recording technique, wherein structures of a first type and of a second type can be identified using the first recording technique and predominantly structures of the first type can be identified using the second recording technique, determination of a region of interest (=ROI) with structures of the second type in the first computed-tomography display data record, determination of relative coordinates of the ROI relative to other significant structures of the first type in the first computed-tomography display data record, determination of the position of significant structures of the first type which match the first display data record in the at least one second computed-tomography display data record, calculation of the position of the ROI in the at least one second computed-tomography display data record on the basis of the positions of the structures of the first type in the second computed-tomography display data record, and representation of the ROI in the at least one second computed-tomography display data record.

For example, the first recording technique may be a recording technique using contrast agent in order to display structures of the second type better. For example, this may be an agent which is absorbed to an increased extent in comparison to the surrounding tissue or else a radioactive agent which produces the contrast by itself emitting radiation.

In one particularly advantageous embodiment, an X-ray CT system can be used for the first recording technique, in which case it is also possible to use at least two different X-ray energy spectra for the scan, thus allowing structures to be displayed better. When using a CT system, it is also possible to use a higher dose for the first recording technique, so that the structures in the CT scans have less noise superimposed on them and a scan with better contrast is made available. According to one particular embodiment of the method, the at least two different X-ray energy spectra may also be produced by different X-ray tubes.

Particularly when an organ or organs is or are involved, it may be particularly advantageous at least to also use a magnetic resonance imaging system and/or a PET system as the first recording technique. Systems such as these make it possible to distinguish very well between soft tissue structures or else simple marking of specific tissue types, for example tumor tissue, although these can be operated only to a restricted extent during the actual intervention, because of the size of the equipment required and the relatively small amount of space available around the patient because of this. However, it should be noted that it is nevertheless within the scope of at least one embodiment of the invention for somewhat more cumbersome systems such as these also to be used for the second recording technique.

The inventor therefore also proposes, in at least one embodiment, that the second recording technique use an X-ray CT system, in particular a C-arc appliance. Alternatively, a magnetic resonance imaging system or else a supplementary PET system can also be used for the second recording technique.

Furthermore, for example, it is possible to define the region of interest (ROI) by segmentation of a structure of the second type in the first computed-tomography display data record. Alternatively or additionally, this ROI may be defined by a manually entered geometric object, for example by a cylinder, a sphere and an ellipsoid or a cuboid for three-dimensional displays, or a circle, a rectangle or an ellipse for two-dimensional displays, in the first computed-tomography display data record. This may be done, for example, by a manual entry by the user on the computed-tomography display. However, automatic entry in the image is also possible by automatic identification of lesions and inclusion of these lesions by using the predetermined geometric figures.

Furthermore, the method according to at least one embodiment of the invention proposes that the ROI be represented in the at least one second computed-tomography display data record by superimposing the representation of the ROI in the first CT display data record on the second CT display data record. This means that the representation of the ROI is cut out of the first CT display data record, and only this area and not the rest of the image is represented in the second computed-tomography display data record.

By way of example, the ROI can be represented in the at least one second computed-tomography display data record by colored emphasis of the ROI, or else it is possible for the ROI to be indicated as a wire model in the at least one second CT display data record.

A further advantage of the method according to at least one embodiment of the invention is that it is now possible to identify expansions and contractions in the relative positions of the structures of the first type, and for the ROI represented in the second computed-tomography display data record likewise to be expanded or contracted for the stretches and compressions that have been found, thus allowing matching to slightly changed recording situations.

In a corresponding manner to at least one embodiment of the method described above, the inventor also proposes a computed-tomography system or an assembly of different computed-tomography systems with a control and computation unit which has memory for programs and data, with the memory containing program code which carries out the method according to at least one embodiment of the invention as described above during operation.

BRIEF DESCRIPTION OF THE DRAWINGS

The invention will be described in more detail in the following text with reference to one example embodiment and with the aid of the figures, in which the only features illustrated are those necessary for understanding of embodiments of the invention. In this case, the following reference symbols are used: 1: CT system; 2: first X-ray tube; 3: first detector; 4: second X-ray tube (optional); 5: second detector (optional); 6: gantry housing; 7: patient; 8: movable patient couch; 9: system axis; 10: control and computation unit; 11: program memory; 12: contrast agent pump; 13: EKG line; 14: data and control line; 15: control line; 16.1: first computed-tomography display data record; 16.2: second computed-tomography display data record; 17: ROI; 18.$x$: structures of the first type; 19: lesions/structure of the second type; 20: liver tissue; $Prg_x$: computer programs.

In the figures, in detail.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

In one example specific variant of the method, the method according to an embodiment of the invention is subdivided into two basic sections:

In the first section, before the intervention, a complex examination is carried out, for example using contrast agent, and is used as the planning basis for a CT intervention. By way of example, during this planning examination, the user marks a lesion enriched with contrast agent as the ROI. The workflow can be assisted by a segmentation algorithm. The user can then, for example, mark the ROI just by clicking on the lesion, therefore saving manual entry. The system stores the coordinates of the ROI.

In principle, on the one hand, this planning can be carried out immediately before action on the CT console, or else on a separate workstation on the basis of an initial examination. In the latter case, the information is transferred digitally to the CT console in order to be made available, if required, during the intervention.

In the second section, during the intervention, updated image data is available after a first native intervention scan, in which data the ROI has been defined. The previously produced planning scan can be registered using software. The workflow can be improved by using automatic registration algorithms.

The ROI defined in the planning phase is overlaid in translucent form on the registered image data. Once the user is certain of the correct position, or has matched this to the current position manually or automatically on the basis of landmarks, it is then possible to display just the native scan together with the translucent volume of interest, following an input command.

The transparency of the ROI can in each case be matched to the current situation by the user as required, or automatically.

The method can be repeated as often as required during an intervention. In order to improve the workflow, all the adaptations made by the user are in each case preserved, so that only minor corrections need be made, for example as a result of breathing movements.

Figure 1:
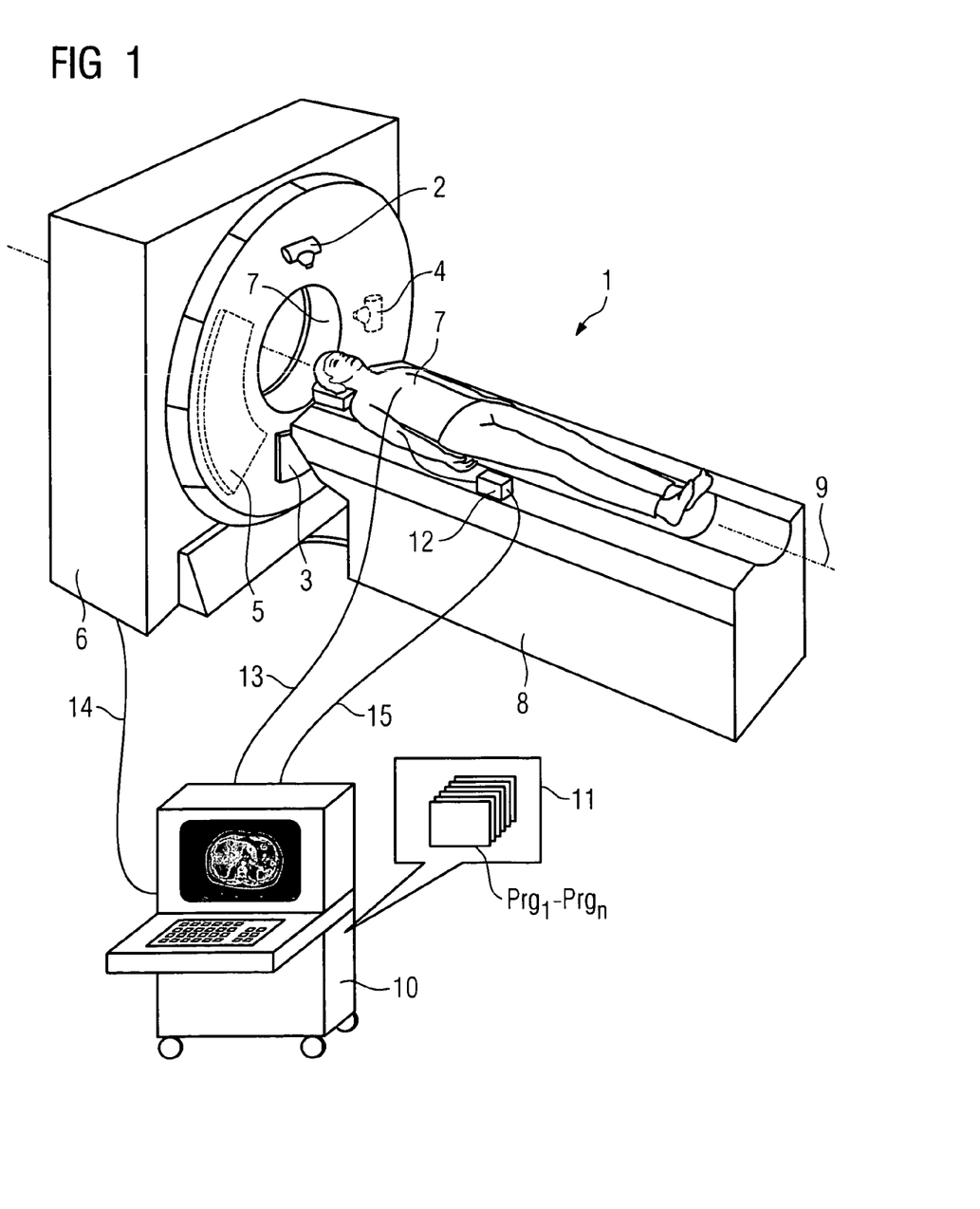
FIG. 1 shows a CT system according to an embodiment of the invention.

FIG. 1 shows an example of a CT system which can be used to carry out the method according to the invention, in which, in this case, different variants of possible CT systems with one or two X-ray detector system or systems and/or with a contrast agent pump are shown on one illustration.

The illustrated CT system has a gantry housing 6 in which a first X-ray tube 2 and a first detector 3, opposite it, are arranged on a gantry which is not shown in any more detail. An additional, second X-ray tube 4 with a detector 5 opposite it, which may be used optionally, is shown by dashed lines. The patient 7 is located on a patient couch 8, by means of which he can be moved sequentially or continuously through the measurement area of the X-ray detector system or systems during the scan, thus making it possible to carry out a sequential circular scan or a spiral scan.

During the scan, by way of example, an EKG can also be recorded and, if required, can be used to control cardiac records via an EKG data line 13, by means of the control and computation system 10 and with the aid of appropriate programs $Prg_1$ to $Prg_n$ in the data memory 11. The system is controlled via the control and data line 14, via which the detector data is also passed to the control and computation unit and is reconstructed, using known methods, by reconstruction to form CT slice images or CT volume displays. The control and computation unit 10 can also carry out any contrast agent injection that may be required, in accordance with the prior requirements, by means of a contrast agent pump 12, so that it is possible to see structures in the CT which can be displayed only with difficulty in CT scans without the use of contrast agent. Alternatively or in addition to the contrast agent, it is also possible to use different X-ray spectra for the scan, thus also improving the capability to identify structures, lesions or tumors.

In a manner corresponding to the method already described above, the patient 7 is scanned using a relatively complex recording technique before the start of an intervention, so that any lesions, tumors or other regions of particular interest on the CT display can be identified. One such display is shown by way of example in FIG. 2, which shows a two-dimensional CT scan 16.1 produced using a method with a complex recording technique, so that a lesion 19 in the liver tissue 20 of a patient is shown here. It should be noted that the illustrated figures contain just two to three black/white representations without gray-scale values although, in practice, gray-scale images, as known by those skilled in the art, are, of course, used.

Figure 2:
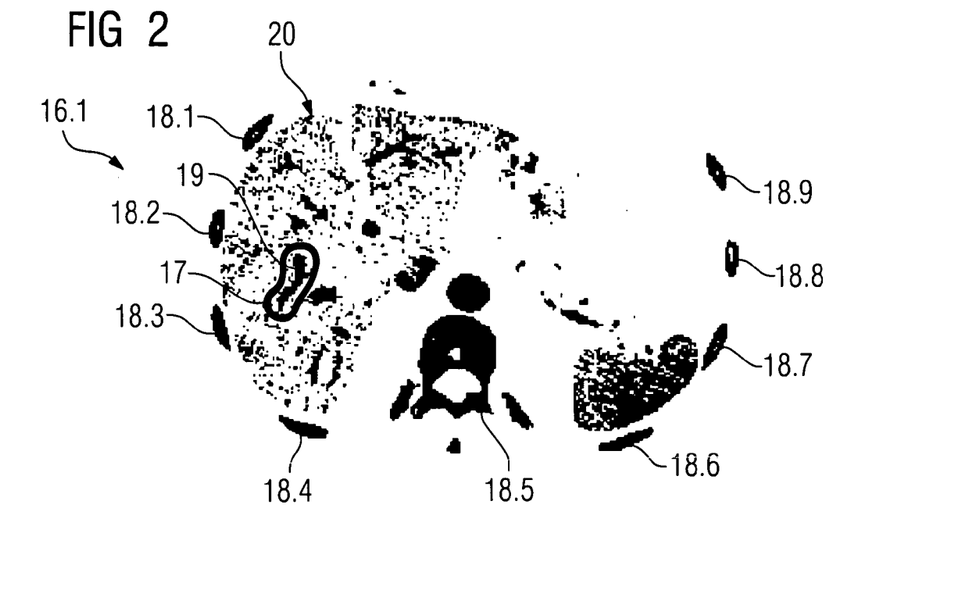
FIG. 2 shows a two-dimensional CT display comprising a first CT display data record with structures of the first type and second type.

According to an embodiment of the invention, the user can now mark an ROI 17 by an appropriate boundary, or else this can be done automatically by an appropriate computation program. The relative position of this ROI 17 can then be determined with respect to structures of the first type 18.1 to 18.9. For example, structures such as these of the first type can be emphasized in such a way that they exceed specific Hounsfield limit units so that it is in fact possible to see in the scan using a relatively complex recording technique that these structures are also clearly evident with the less complex recording technique.

Figure 3:
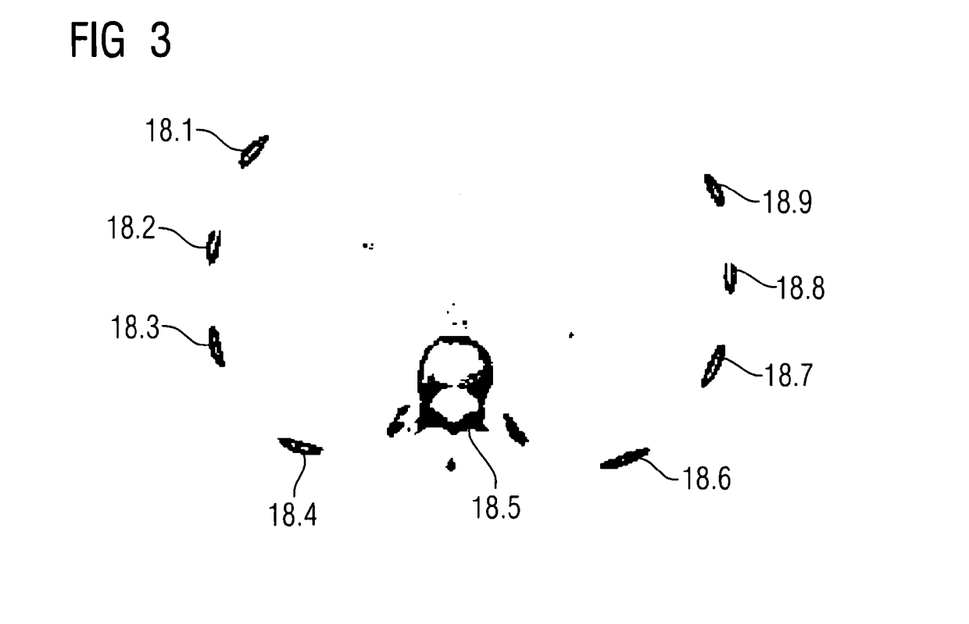
FIG. 3 shows a two-dimensional CT display of the structures of the first type from a second CT display data record.

Structures such as these of the first type 18.1-18.9 are emphasized in FIG. 3. By way of example, structures such as these can be made visible by reproducing just Hounsfield limit units above a specific threshold value in the display.

Figure 4:
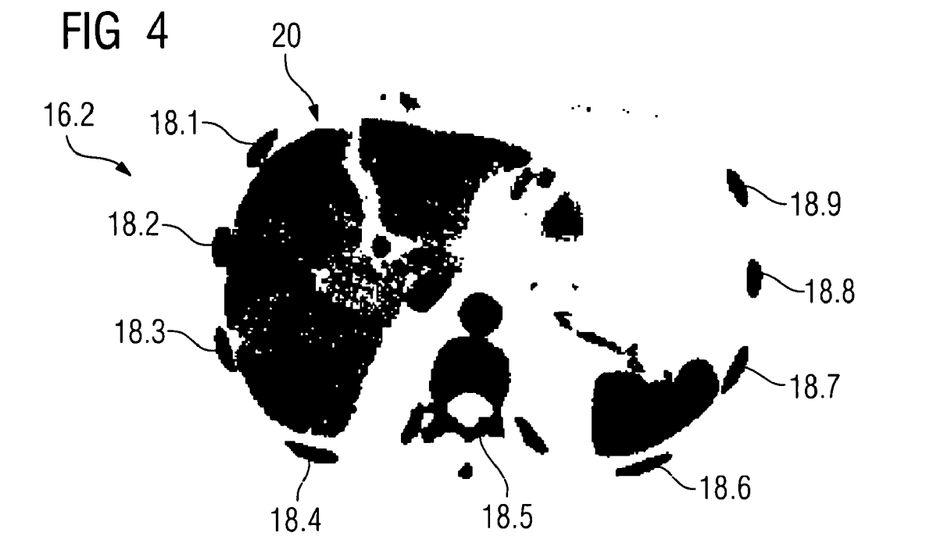
FIG. 4 shows a two-dimensional CT display comprising a second CT display data record, in which structures of the second type cannot be seen.

FIG. 4 now shows a CT scan 16.2 using a simpler recording technique, for example without contrast agent or just with a single X-ray spectrum, and/or using a low dose. As can be seen from the illustration, although it is possible to identify the position of the liver tissue 20 overall and structures of the first type, in this case the bone sections 18.1-18.9, it is virtually impossible to distinguish between structures within the liver tissue 20, so that the user can either not identify a specific target region, or no longer sees regions to be avoided, during an intervention.

Figure 5:
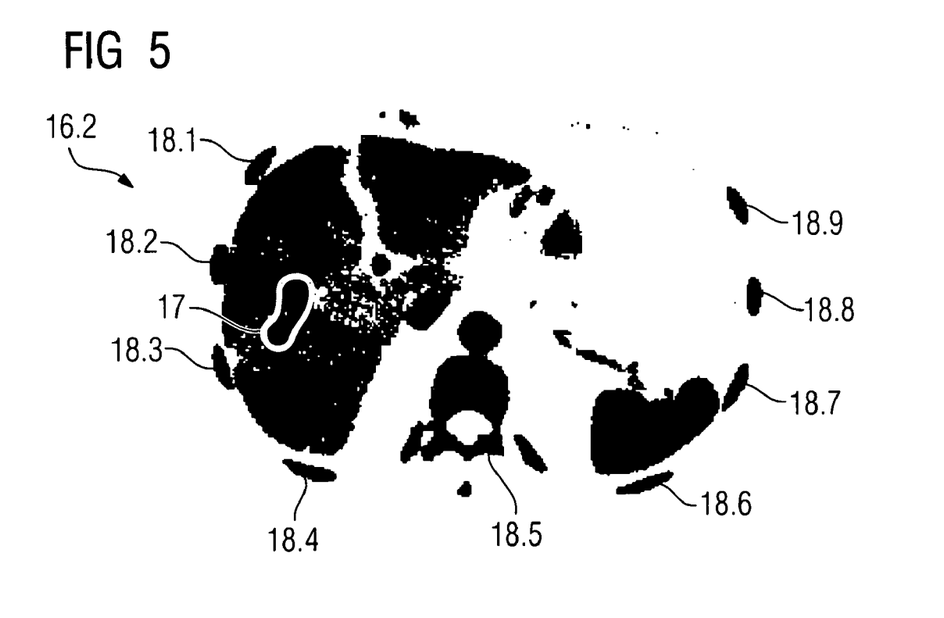
FIG. 5 shows a two-dimensional CT display comprising a second CT display data record, in which structures of the second type cannot be seen, but with a schematically illustrated ROI.

In accordance with an embodiment of the invention, FIG. 5 additionally shows the ROI 17, in principle corresponding to FIG. 4, that is to say showing a CT display 16.2 based on a simple recording technique, in which case its position has been determined relative to the structures of the first type 18.1 to 18.9. It is now possible to carry out the intervention by using a conservative recording technique with a relatively low recording power, with the user nevertheless having reliable knowledge about the position of predetermined regions 17.

Although only CT scans are shown in the figures illustrated by way of example, the invention also covers computed-tomography examinations across different systems. For example, MRI scans or PET scans together with CT scans or vice versa can also be dealt with in a corresponding manner to an embodiment of the method described above.

Thus, in summary, an embodiment of the invention provides a method and a computed-tomography system or a computed-tomography system assembly for displaying computed-tomography records, in which a first computed-tomography display data record is used to display structures of a first and second type by way of a complex recording technique, with a region of interest with structures of the second type being marked there and with relative positions of the structures being determined, and with a second computed-tomography display data record subsequently being produced by way of a simpler recording technique, in which only structures of the first type can be identified, and the structures of the second type are made visible on the basis of the known relative positions with respect to the visible structures of the first type or at least their position, or a surrounding boundary in this display.

It is self-evident that the features of embodiments of the invention mentioned above may be used not only in the respectively stated combination but also in other combinations or on their own without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for displaying computed-tomography scans by and with a computation unit, comprising:
    generating a first display data record using a first recording technique and at least one second computed-tomography display data record using a second recording technique different from the first recording technique, such that structures of a first type and of a second type are identifiable using the first recording technique, and structures of the second type are not identifiable using the second recording technique;
    receiving details of a region of interest (ROI) with structures of the second type in the first computed-tomography display data record;
    determining relative coordinates of the ROI relative to other significant structures of the first type in the first computed-tomography display data record;
    determining a position of significant structures of the first type which match the first display data record in the at least one second computed-tomography display data record, the second computed-tomography display data record being generated during a CT-based intervention procedure;
    calculating the position of the ROI in the at least one second computed-tomography display data record based on the positions of the structures of the first type in the second computed-tomography display data record; and
    representing the ROI in at least one second computed-tomography display data record.

2. The method as claimed in claim 1, wherein the first recording technique uses an X-ray CT system.

3. The method as claimed in claim 1, wherein the first recording technique uses at least two different X-ray energy spectra for scanning and to improve a display of structures of the second type.

4. The method as claimed in claim 1, wherein the first recording technique also uses at least a magnet resonance imaging system.

5. The method as claimed in claim 1, wherein the first recording technique also uses at least a PET system.

6. The method as claimed in claim 1, wherein the second recording technique uses a magnetic resonance imaging system.

7. The method as claimed in claim 1, wherein the ROI is defined by segmentation of a structure of the second type in the first computed-tomography display data record.

8. The method as claimed in claim 1, wherein the ROI is defined by a manually entered geometric object in the first computed-tomography display data record.

9. The method as claimed in claim 1, wherein the ROI is represented in the at least one second computed-tomography display data record by superimposing the representation of the ROI in the first computed-tomography display data record on the second computed tomography display data record.

10. The method as claimed in claim 1, wherein the ROI is represented in the at least one second computed-tomography display data record by colored emphasis of the ROI.

11. The method as claimed in claim 1, wherein the ROI is represented as a wire model in the at least one second computed-tomography display data record.

12. A computed-tomography system assembly, comprising:
at least one control and computation unit including a memory with program code, the program code implementing the method of claim 1 during operation of the at least one control and computation unit.

13. A non-transitory computer readable medium including program segments for, when executed on a computer device, causing the computer device to implement the method of claim 1.

14. The method as claimed in claim 1, wherein the first recording technique uses contrast agent to improve a display of structures of the second type.

15. The method as claimed in claim 14, wherein the first recording technique uses an X-ray CT system.

16. The method as claimed in claim 1, wherein the first recording technique uses a relatively higher radiation dose for each CT display data record than that used for the second recording technique.

17. The method as claimed in claim 16, wherein the at least two different X-ray energy spectra are produced by different X-ray tubes.

18. The method as claimed in claim 1, wherein the second recording technique uses an X-ray CT system.

19. The method as claimed in claim 18, wherein a C-arc appliance is used as the X-ray CT system.

20. A computed-tomography system, comprising:
at least one control and computation unit including a memory with program code, the program code configured to cause the control and computation unit to execute,
generating a first display data record using a first recording technique and at least one second computed-tomography display data record using a second recording technique different from the first recording technique, such that structures of a first type and of a second type are identifiable using the first recording technique, and structures of the second type are not identifiable using the second recording technique;
receiving details of a region of interest (ROI) with structures of the second type in the first computed-tomography display data record;
determining relative coordinates of the ROI relative to other significant structures of the first type in the first computed-tomography display data record;
determining a position of significant structures of the first type which match the first display data record in the at least one second computed-tomography display data record, the second computed-tomography display data record being generated during a CT-based intervention procedure;
calculating the position of the ROI in the at least one second computed-tomography display data record based on the positions of the structures of the first type in the second computed-tomography display data record; and
representing the ROI in at least one second computed-tomography display data record.

* * * * *

UNITED STATES PATENT AND TRADEMARK OFFICE
CERTIFICATE OF CORRECTION

| | | |
|---|---|---|
| PATENT NO. | : 8,358,874 B2 | Page 1 of 1 |
| APPLICATION NO. | : 12/000476 | |
| DATED | : January 22, 2013 | |
| INVENTOR(S) | : Haras | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1169 days.

Signed and Sealed this
Eighteenth Day of November, 2014

Michelle K. Lee
*Deputy Director of the United States Patent and Trademark Office*